(12) United States Patent
Frater et al.

(10) Patent No.: US 7,683,190 B2
(45) Date of Patent: Mar. 23, 2010

(54) PROCESS FOR THE PREPARATION OF OPTICALLY-ACTIVE COMPOUNDS

(75) Inventors: Georg Frater, Winterthur (CH); Urs Mueller, Duebendorf (CH)

(73) Assignee: Givaudan SA, Vernier (CH)

( * ) Notice: Subject to any disclaimer, the term of this patent is extended or adjusted under 35 U.S.C. 154(b) by 304 days.

(21) Appl. No.: 11/572,834

(22) PCT Filed: Jul. 26, 2005

(86) PCT No.: PCT/CH2005/000442

§ 371 (c)(1),
(2), (4) Date: Apr. 27, 2007

(87) PCT Pub. No.: WO2006/010287

PCT Pub. Date: Feb. 2, 2006

(65) Prior Publication Data

US 2008/0064886 A1    Mar. 13, 2008

(30) Foreign Application Priority Data

Jul. 30, 2004    (GB) .................................. 0417063.5

(51) Int. Cl.
*C07D 307/00*    (2006.01)
(52) U.S. Cl. ..................................... 549/469
(58) Field of Classification Search .................. 549/469
See application file for complete search history.

(56) References Cited

U.S. PATENT DOCUMENTS 4,209,529 A    6/1980    Tomiyama

FOREIGN PATENT DOCUMENTS

| EP | 0506776 A | 10/1992 |
|---|---|---|
| EP | 0550889 A1 | 7/1993 |
| GB | 1187395 A | 4/1970 |
| WO | 9109852 A1 | 7/1991 |
| WO | 9321174 A1 | 10/1993 |
| WO | 2004013069 A1 | 2/2004 |

OTHER PUBLICATIONS

Saito et al., Chemistry Letters (1984), (4), 591-4.*
Aryku et al. STN Document No. 116:129310, Abstrct of Khimiya Prirodnykh Soedinenii (1991), (3), 343-9.*
International Search Report dated Oct. 28, 2005 for application PCT/CH2005/000442.
Written Opinion of the International Searching Authority for application PCT/CH2005/000442.
Kazuaki Ishihara: "Enantio- and Diastereoselective Stepwise cyclisation of Polyprenoids induced by Chiral and achiral LBAs. A new Entry to ( - )Ambrox) . . . ." J. Am. Chem. Soc., vol. 124, No. 14, Mar. 16, 2002. p. 3647-3655, XP002351724; Columbus Ohio; the whole document; p. 3653, col. 2, last paragraph—p. 3654, paragraph First.
Snowden R L et al: "Internal Nucleophilic Termination in Acid-Mediated Polyene Cyclisations: Synthetic Access to Methyl Homologs of (_)-Ambrox(R) and Its Diastereoisomers"; 1993, Helvetica Chimica Acta. Basel, CH, pp. 1608-1618, XP000561989; ISSN: 0018-019X; the whole document.
Buechi G et al: "The Synthesis of Racemic Ambrox"; 1989, Helvetica Chimica Acta, Verlag Helvetica Chimica Acta. Basel, CH, pp. 996-1000, XP009055121; ISSN: 0018-019X; cited in the application; the whole document; p. 997-p. 999; examples 10, 13.
Saito A et al: "Cyclization of E, E-Homofarnesic Acid and Its Related Compounds"; 1984, Chemistry Letters, Chemical Society of Japan. Tokyo, JP, pp. 591-594, XP009055120; ISSN: 0366-7022; the whole document.
Search Report issued by The Patent Office in Great Britain dated Nov. 25, 2004 for application GB0417063.5.
Chemical Abstract 79:61866 & G. Coppi et al, Arzneimittel-Forschung, (1973), 23(5), 693-700; See compound with registry No. 38911-59-0.

* cited by examiner

*Primary Examiner*—D. Margaret Seaman
*Assistant Examiner*—Nizal S Chandrakumar
(74) *Attorney, Agent, or Firm*—Norris McLaughlin & Marcus, PA (57) ABSTRACT

A method of preparing enatiomerically enriched 3a,6,6,9a-tetramethyl-dodecahydro-naphtho[2,1-b]furan, formula (I), from (E,E)-homofarnesic acid or (E)-monocyclohomofarnesic acid by (a) reacting firstly with a chiral alcohol, (b) reacting the product of (a) with an acid to cause a first cyclization, (c) producing an alcohol by reacting the product of (b) with a reducing agent and (d) causing a second cyclization by reacting the product of (c) with an acid. The product of this process gives a mixture of both enantiomers with one in excess.

1 Claim, 3 Drawing Sheets

PROCESS FOR THE PREPARATION OF OPTICALLY-ACTIVE COMPOUNDS

This is an application filed under 35 USC 371 of PCT/CH2005/000442.

This invention relates to a method of preparing optically-active 3a,6,6,9a-tetramethyl-dodecahydro-naphtho[2,1-b]furan and to an optically-active 3a,6,6,9a-tetramethyl-dodecahydro-naphtho[2, 1-b]furan prepared thereby.

(−)-(3aR,5aS,9aS,9bR)-3a,6,6,9a-Tetramethyl-dodecahydro-naphtho[2,1-b]furan is a naturally occurring ambergris odorant widely used in perfumery. For convenience, the compound will hereinafter be referred to as "TDNF", with the various isomers being designated as (+)-TDNF, (−)-TDNF and (rac)-TDNF. (−)-TDNF can be obtained by chemical transformation of the naturally-occurring product sclareol (Perfumer & Flavorist 2004, Vol. 29, March/April, p. 34). This product is subject to supply fluctuations according to harvest, and shortages lead to increased prices. This has led to a search for completely synthetic processes for the preparation of (−)-TDNF.

Entirely synthetic processes for (rac)-TDNF have been described, e.g. the synthesis starting from dihydro-β-ionone [G. Büichi, H. Wüest, *Helv. Chim. Acta* 1989, 72, 996].

As (−)-TDNF is described as more ambery and as much as two to three times more powerful than (+)-TDNF (Perfumer & Flavorist 2004, Vol. 29, March/April, p. 34), a synthetic process leading to a TDNF quality enriched in (−)-TDNF is of great importance. This has been achieved by classical optical resolution of racemic [(1R,S,2R,S,4aS,R,8aS,R)-2-hydroxy-2,5,5,8a-tetramethyldecahydronaphtalen-1-yl]acetic acid using chiral amines as the resolving agents. Asanuma et al. describe the optical resolution using 1-aryl-ethylamines as the optical resolving agent [G. Asanuma, Y. Tamai, Eur. Pat. Appl. 550889 (1993)], Koga et al. use 1,3-amino-alcohols as resolving agents (Tetrahedron Asymmetry 1998, 9, 3819), and Huboux applied (R,R)-pseudoephedrine as the chiral auxiliary (A. Huboux, PCT Int. Appl. WO 2004013069, Dec. 2, 2004).

However, these processes suffer from the disadvantage of a low yield of (−)-TDNF, which is maximal 50%, as the separated (+)-TDNF is less interesting as a fragrance ingredient.

Therefore there is a need for a more efficient process capable of providing optically enriched TDNF.

It has now been found that it is possible to prepare TDNF that has in excess of 50% of a desired isomer, particularly the desirable (−)-isomer. The invention therefore provides a method of preparation of a TDNF mixture having a proportion of one isomer greater than 50%, comprising the steps of:

1. reacting a compound selected from (E,E)-homofarnesic acid and (E)-monocyclohomofarnesic acid with a chiral alcohol of formula R*OH;
2. reacting the result of step 1 with an acid to form one of the compounds of formula V 3. reacting the result of step 2 with a reducing agent, to form an alcohol; and 4. treating the alcohol of step 3 with an acid to form compounds of the formulae VI and VII (−)-TDNF

(+)-TDNF

The invention additionally provides a TDNF mixture, in which the proportion of one of the isomers is in excess of 50%.

(E,E)-Homofarnesic acid [(E,E)-4,8,12-trimethyl-trideca-3,7,11-trienoic acid] can be prepared, for example, as described in: K. Ishihara, H. Ishibashi, H. Yamamoto, Hisashi, *J. Am. Chem. Soc.* 2002, 124, 3647-3655; A. Saito, H. Matsushita, H. Kaneko, *Chem. Lett.* 1984, 4, 591-594.

(E)-Monocyclohomofarnesic acid [(E)-4-Methyl-6-(2,6,6-trimethyl-cyclohex-1-enyl)-hex-3-enoic acid] can be prepared, for example, as described in: R. L. Snowden, J. C. Eichenberger, W. Giersch, W. Thommen, K. H. Schulte-Elte, *Helv. Chim. Acta* 1993, 76, 1608-1618.

The chiral alcohol R*OH may be any such chiral alcohol known to the art. The nature of the process dictates that the group R* should not be too large, and the skilled person can easily select a suitable group R*. The preferred chiral alcohols for use in this invention have the general formula:

wherein:

$R^1$, $R^2$ and $R^3$ are individually selected from H, alkyl, alkenyl, alkinyl, cycloakyl, cycloalkenyl, cycloalkylalkyl, alkylcycloakyl, cycloakylalkenyl, alkylcycloalkenyl, aryl, alkylaryl, alkenylaryl, arylalkyl, arylalkenyl and cyclic moieties of these types that additionally comprise at least one heteroatom such as N, O, S, Si, $R^1$, $R^2$ and $R^3$ being optionally substituted by at least one substituent, such as OH, CHO, $CO_2H$, $CO_2R^4$, $CONH_2$, $CONHR^5$, $CONR^5R^6$, $NO_2$, CN, wherein $R^4$, $R^5$ and $R^6$ are independently $C_1$-$C_6$ alkyl; with the proviso that the residues $R^1$, $R^2$ and $R^3$ are different. Most preferably $R^1$=H and $R^2$ and $R^3$ have the meaning as described above.

It has been found that some of the reaction products of (E,E)-homofarnesic acid and (E)-monocyclohomofarnesic acid with a chiral alcohol of formula R*OH, as hereinabove described, are novel compounds in their own right. The invention therefore also provides a compound selected from the group consisting of compounds of formula III and formula IV:

wherein R* is the residue of a chiral alcohol R*OH.

Typical examples of such compounds include those prepared in Examples 1, 2, 6 and 7 below.

The invention also provides the use of a compound of formula III or formula IV as an intermediate for preparing a mixture of TDNF, in which the proportion of (−)-TDNF is in excess of 50%. The invention further provides the use of a compound of formula III or formula IV as an intermediate for preparing a mixture of TDNF, in which the proportion of (+)-TDNF is in excess of 50%.

Cyclisation of the resulting ester is brought about by reaction with an acid. Examples of suitable cyclisation agents include mineral acids, organic acids and Lewis acids. Examples of suitable mineral acids include phosphoric acid, sulphuric acid and perchloric acids, heteropolyacids such as $H_3[P(W_3O_{10})_4]$, acid resins such as Dowex™ 50 or Amberlyst™. Examples of suitable protonic acids include hydrohalide acids such as hydrogen chloride and hydrogen bromide. Examples of organic acids include acetic acid, trifluoroacetic acid, methanesulphonic acid and chlorosulphonic acid. These named acids are purely exemplary. It is also possible to use mixtures of the abovementioned acids.

Non-restrictive examples of suitable Lewis acids include products such as $AlCl_3$, $TiCl_4$, $SnCl_4$ and $MeAlCl_2$.

The cyclisation is carried out in an inert organic solvent. The selection of a suitable solvent is well known within the skill of the art, but suitable examples include petroleum ether, halogenated hydrocarbons such as chloroform, dichloromethane and trichloroethane, aromatic hydrocarbons such as benzene, toluene and nitrobenzene, ethers such as diethyl ether, methyl tertbutyl ether and tetrahydrofuran, esters, nitrogen containing hydrocarbons such as nitromethane, nitropropane and acetonitrile.

The transformation of the chiral ester obtained from the second step to the alcohol is carried out with a reducing agent. Any reducing agent that is capable performing the desired transformation may be used, and the skilled person will readily be able to identify a suitable reducing agent. Non-limiting examples of suitable reducing agents are hydride sources such as lithium aluminium hydride, sodium borohydride, Red-Al and silanes. The reduction is carried out in an inert solvent, the selection of which will be evident for a skilled person in the art.

The second cyclisation necessary to form TDNF is carried out by firstly reacting the product of the first cyclisation described hereinabove with a reducing agent to form an alcohol, and secondly reacting this alcohol with an acid to cause the cyclisation. Examples of suitable cyclisation agents include mineral acids and organic acids. Examples of suitable mineral acids include phosphoric acid, sulphuric acid and perchloric acids, heteropolyacids such as $H_3[P(W_3O_{10})_4]$, acid resins such as Dowex™ 50 or Amberlyst™. Examples of suitable protonic acids include hydrohalide acids such as hydrogen chloride and hydrogen bromide. Examples of organic acids include acetic acid, trifluoroacetic acid, methanesulfonic acid and chlorosulphonic acid. These named acids are purely exemplary.

It is also possible to use mixtures of the abovementioned acids.

The reaction scheme is as shown below:

-continued 1) reducing agent/inert organic solvent
2) H⁺/inert organic solvent

VI  
(-)-TDNF

VII  
(+)-TDNF

The reaction is easily carried out under mild conditions. As mentioned hereinabove, it has the additional advantage of producing a mixture of isomers VI and VII in which the proportion of VI is in excess of 50%. If desired, a mixture of isomers VI and VII in which the proportion of VII is in excess of 50%, can be prepared.

The invention is now further described with reference to the following non-limiting examples, which describe preferred embodiments, and to the accompanying drawings, which are gas chromatograms (GC), each carried out using a chiral column (Hydrodex-β-6TBDM, 25 m×0.25 mm, 170° C. isotherm, 60 kPa H$_2$, split 1:50).

EXAMPLE 1

Synthesis of (E,E)-4,8,12-Trimethyl-trideca-3,7,11-trienoic acid (R)-methoxycarbonyl-phenyl-methyl ester To a solution of 12.5 g (50 mmol) (E,E)-4,8,12-trimethyl-trideca-3,7,11-trienoic acid (isomeric purity of 95%) [K. Ishi-hara et al., *J. Am. Chem. Soc.* 2002, 124, 3647-3655] in 100 ml methyl tert-butyl ether (MTBE) were added at r.t. 8.35 g (50 mmol) (R)-(−)-mandelic acid methyl ester, $[\alpha]_D$=−147.3 (c=1.0, MeOH), and 1.5 g 4-dimethylaminopyridine (DMAP). After stirring for 15 min at 28° C., 10.5 g (51 mmol) N,N'-dicyclohexylcarbodiimide (DCC) were added, during which the temperature raised to 35° C. The reaction mixture was stirred for 1.5 h at 38-40° C., cooled to r.t. and filtered. The resulting solution was concentrated in vacuo. The residue (23.1 g) was purified over 100 g silicagel, elution of the product with hexane/MTBE 1:1. Concentration of the combined fractions in vacuo and drying of the product in high vacuo (50° C./0.08 Torr) afforded 19.5 g (97%) of (E,E)-4,8,12-trimethyl-trideca-3,7,11-trienoic acid (R)-methoxycarbonyl-phenyl-methyl ester (1) in form of a colorless oil.

IR (film): 2918 w, 1746 s, 1214 m, 1141 s, 1046 m.

$^1$H-NMR (400 MHz, CDCl$_3$): δ 1.59 (s, 6H), 1.64 (m, 3H), 1.67 (m, 3H), 2.01-1.93 (m, 2H), 2.15-2.01 (m, 6H), 3.20 (m, 2H), 3.68 (s, 3H), 5.15-5.04 (m, 2H), 5.37 (t, J=7.1 Hz, 1H), 5.93 (s, 1 H), 7.34-7.39 (m, 3H), 7.44-7.48 (m, 2H) ppm.

$^{13}$C-NMR (100 MHz, CDCl$_3$): δ 15.8 (q), 16.3 (q), 17.5 (q), 25.5 (q), 26.3 (t), 26.6 (t), 33.1 (t), 39.4 (t), 39.5 (t), 52.3 (q), 74.3 (d), 114.8 (d), 123.7 (d), 124.2 (d), 127.4 (2d), 128.6 (2d), 129.0 (d), 131.0 (s), 133.7 (s), 135.0 (s), 139.5 (s), 169.1 (s), 171.4 (s) ppm.

MS (ESI-pos): 398 (12, [M]⁺), 249 (28), 149 (72), 121 (72), 69 (100), 41 (32), HR-MS: 398.2461 (C$_{25}$H$_{34}$O$_4^+$; calc. 398.2457).

Optical rotation: $[\alpha]_D$=−66.9 (c=1.08, MeOH).

EXAMPLE 2

Synthesis of (E,E)-4,8,12-Trimethyl-trideca-3,7,11-trienoic acid (S)-methoxycarbonyl-phenyl-methyl ester

2

To a solution of 12.5 g (50 mmol) (E,E)4,8,12-trimethyl-trideca-3,7,11-trienoic acid (isomeric purity of 95%) [K. Ishihara et al., *J. Am. Chem. Soc.* 2002, 124, 3647-3655] in 100 ml MTBE were added at r.t. 8.4 g (50 mmol) (S)-(+)-mandelic acid methyl ester $[\alpha]_D$=+144.9 (c=1.04, MeOH) and 1.5 g DMAP. After stirring for 15 min, 10.5 g (51 mmol) DCC is added, during which the temperature raised to 35° C. The reaction mixture was stirred for 4 h at 35° C., cooled to room temperature and filtered. The resulting solution was concentrated in vacuo to a volume of ca. 50 ml and filtered over 100 g of silicagel. The product was eluted with ca. 600 ml hexane/MTBE 1:1. Concentration of the combined fractions in vacuo and drying of the product in high vacuo (50° C./0.08 Torr) afforded 19.8 g (98%) of (E,E)-4,8,12-Trimethyl-trideca-3,7,11-trienoic acid (S)-methoxycarbonyl-phenyl-methyl ester (2) in form of a colorless oil.

IR(film): 2926 w, 1746 s, 1214 m, 1141 s, 1046 m.

hu 1H-NMR (400 MHz, CDCl$_3$): δ 1.59 (s, 6H), 1.64 (m, 3H), 1.67 (m, 3H), 2.01-1.93 (m, 2H), 2.15-2.01 (m, 6H), 3.20 (m, 2H), 3.68 (s, 3H), 5.15-5.04 (m, 2H), 5.37 (t, J=7.1 Hz, 1H), 5.93 (s, 1 H), 7.34-7.39 (m, 3H), 7.44-7.48 (m, 2H) ppm.

$^{13}$C-NMR (100 MHz, CDCl$_3$): δ 15.8 (q), 16.3 (q), 17.5 (q), 25.5 (q), 26.3 (t), 26.6 (t), 33.1 (t), 39.4 (t), 39.5 (t), 52.3 (q), 74.3 (d), 114.8 (d), 123.7 (d), 124.2 (d), 127.4 (2d), 128.6 (2d), 129.0 (d), 131.0 (s), 133.7 (s), 135.0 (s), 139.5 (s), 169.1 (s), 171.4 (s) ppm.

MS (ESI-pos): 398 (10, [M]$^+$), 249 (28), 149 (61), 121 (70), 69 (100), 41 (29).

HR-MS: 398.2456 ($C_{25}H_{34}O_4^+$; calc. 398.2457).

Optical rotation: $[\alpha]_D$=+60.4 (c=1.07, MeOH).

EXAMPLE 3

Step 1) Synthesis of (R)-Phenyl-[(4aS,8aS)-2-(2,5,5,8a-tetramethyl-3,4,4a,5,6,7,8,8a-octahydro-naphthalen-1-yl)-acetoxy]-acetic acid methyl ester (3) and (R)-Phenyl-[(4aS,8aS)-2-(2,5,5,8a-tetramethyl-1,4,4a,5,6,7,8,8a-octahydro-naphthalen-1-yl)-acetoxy]-acetic acid methyl ester (4)

3

4

Under an atmosphere of argon 4.14 g (10.4 mmol) (E,E)-4,8,12-Trimethyl-trideca-3,7,11-trienoic acid (R)-methoxycarbonyl-phenyl-methyl ester (1), prepared from homofarnesic acid of 85% isomeric purity as described in example 1, were dissolved in 30 ml CH$_2$Cl$_2$. The solution was cooled to −90° C. and under cooling with liquid nitrogen 2.33 ml (35 mmol) chlorosulphonic acid was added such that the reaction temperature did not exceed −80° C. After the complete addition the reaction mixture was kept at −85° C. for 30 min and then poured rapidly onto 100 ml H$_2$O. The mixture was neutralized by addition of solid KHCO$_3$ and extracted 2× with MTBE. The combined organic phases were washed 2× with brine, dried over MgSO$_4$ and concentrated in vacuo. The crude residue (3.9 g) was purified by flash chromatography (70 silica gel, hexane/MTBE 1:1) to afford 1 g (24%) of a 4:1 mixture (NMR analysis) of ester 3 and 4.

Step 2) Synthesis of (4aS,8aS)-2-(2,5,5,8a-Tetramethyl-3,4,4a,5,6,7,8,8a-octahydro-naphthalen-1-yl)-ethanol (5) and (4aS,8aS)-2-(2,5,5,8a-Tetramethyl-1,4,4a,5,6,7,8,8a-octahydro-naphthalen-1-yl)-ethanol (6)

5

6

To a suspension of 0.5 g (13 mmol) LiAlH$_4$ in 20 ml THF was added at 20° C. a solution of 1.0 g (2.5 mmol) ester mixture 3/4 (example 3, step 1) dissolved in 20 ml THF, during which the temperature raised to 40° C. The reaction mixture was heated at reflux for 30 min, cooled to 40° C. and carefully hydrolysed with 0.5 ml H$_2$O. Then 0.5 ml 15% NaOH solution was added and the mixture stirred for 5 min. After addition of 1.5 ml H$_2$O stirring was continued for 30 min and the mixture was filtered. The residue was washed with MTBE, the combined organic phases were dried over MgSO$_4$, concentrated in vacuo to give 0.93 g crude product as a mixture of alcohols 5/6 (contained ca. 30% of 1-phenyl-ethane-1,2-diol) that was directly used in the next step without further purification.

Alcohol 5:

MS (ESI-pos): 236 (54, [M]$^+$), 221 (86), 191 (89), 177 (50), 163 (30), 151 (42), 135 (38), 125 (70), 107 (68), 95 (100), 81 (57), 69 (56), 55 (46), 41 (53).

Alcohol 6:

MS (ESI-pos): 236 (12, [M]$^+$), 221 (6), 177 (6), 124 (37), 112 (47), 109 (100), 94 (24), 81 (28), 69 (15), 55 (14), 41 (17).

Step 3) Synthesis of (−)-TDNF (7) and (+)-TDNF (8)

To a solution of 0.93 g alcohol mixture 5/6 (example 3, step 2) in 15 ml CH$_2$Cl$_2$ was added at r.t. and under an atmosphere of nitrogen 0.3 ml methanesulphonic acid. After stirring for 15 min another 0.3 ml portion of methanesulphonic acid was added. Stirring was continued for 15 min and the mixture poured onto 50 ml satd. KHCO$_3$ solution. The aqueous phase was extracted 2× with MTBE, the combined organic phases were washed with satd. KHCO$_3$ solution, dried over MgSO$_4$ and concentrated in vacuo. The crude product (0.9 g) was purified by flash chromatography (50 g silicagel, hexane/MTBE 49: 1) to afford 0.43 g (70%) of a white solid. Analysis using a chiral column (Hydrodex-B-6-TBDM, 25 m×0.25 mm, 170° C. isotherm, 60 kPa H$_2$, split 1:50) indicated a 44:56 mixture of (−)-TDNF (7) and (+)-TDNF (8), which is equal to an enantiomeric excess of 12%.

EXAMPLE 4

Step 1) Synthesis of (S)-Phenyl-[(4aS,8aS)-2-(2,5,5,8a-tetramethyl-3,4,4a,5,6,7,8,8a-octahydro-naphthalen-1-yl)-acetoxy]-acetic acid methyl ester (9) and (S)-Phenyl-[(4aS,8aS)-2-(2,5,5,8a-tetramethyl-1,4,4a,5,6,7,8,8a-octahydro-naphthalen-1-yl)-acetoxy]-acetic acid methyl ester (10)

Under an atmosphere of argon 5.5 g (14 mmol) (E,E)-4,8,12-Trimethyl-trideca-3,7,11-trienoic acid (s)-methoxycarbonyl-phenyl-methyl ester (2), prepared from homofarnesic acid of 85% isomeric purity as described in example 2, was dissolved in 100 ml CH$_2$Cl$_2$. The solution was cooled to −90° C. and under cooling with liquid nitrogen 3.3 ml (2.5 eq.) chlorosulphonic acid was added such that the reaction temperature did not exceed −85° C. After complete addition the reaction mixture was kept at −80° C. for 30 min and then poured rapidly onto 50 ml H$_2$O. The mixture was neutralized by addition of 50 ml satd. KHCO$_3$ solution and extracted 2× with hexane. The combined organic phases were washed 2× with brine, dried over MgSO$_4$ and concentrated in vacuo. The crude residue (4.2 g) was purified by flash chromatography (100 silicagel, hexane/MTBE 8:2) to afford 1.8 g (32%) of a 4:1 mixture of ester 9/10 (NMR analysis).

Step 2) (4aS,8aS)-2-(2,5,5,8a-Tetramethyl-3,4,4a,5,6,7,8,8a-octahydro-naphthalen-1-yl)-ethanol (5) and (4aS,8aS)-2-(2,5,5,8a-Tetramethyl-1,4,4a,5,6,7,8,8a-octahydro-naphthalen-1-yl)-ethanol (6)

To a suspension of 1.0 g (25 mmol) LiAlH$_4$ in 50 ml THF was added at 20° C. a solution of 1.8 g (4.5 mmol) ester mixture 9/10 (example 4, step 1) dissolved in 50 ml THF, during which the temperature raised to 40° C. The reaction mixture was heated at reflux for 1 h, cooled to 40° C. and carefully hydrolysed with 1 ml H$_2$O. Then 1 ml 15% NaOH solution was added and the mixture stirred for 5 min. After addition of 3 ml H$_2$O stirring was continued for 30 min and the mixture was filtered. The residue was washed with MTBE, the combined organic phases were dried over MgSO$_4$ and concentrated in vacuo to give 1.45 g crude product as a mixture of 5/6 (contained ca. 30% of 1-phenyl-ethane-1,2-diol) that was directly used in the next step without further purification.

Step 3) Synthesis of (−)-TDNF (7) and (+)-TDNF (8)

To a solution of 1.45 g alcohol mixture 5/6 in 15 ml CH₂Cl₂ was added at r.t. and under an atmosphere of nitrogen 1 ml methanesulphonic acid. The mixture was stirred for 15 min and poured onto 50 ml satd. KHCO₃ solution. The aqueous phase was extracted 2× with MTBE, the combined organic phases were washed with satd. KHCO₃ solution, dried over MgSO₄ and concentrated in vacuo. The crude product (1.3 g) was purified by flash chromatography (50 g silicagel, hexane/MTBE 49:1) to afford 0.4 g (39%, 2 steps) of a white solid. Analysis using a chiral column (Hydrodex-B-6-TBDM, 25 m×0.25 mm, 170° C. isotherm, 60 kPa H₂, split 1:50) indicated a 56:44 mixture of (−)-TDNF (7) and (+)-TDNF (8), which is equal to an enantiomeric excess of 12%.

EXAMPLE 5

Figure 1:
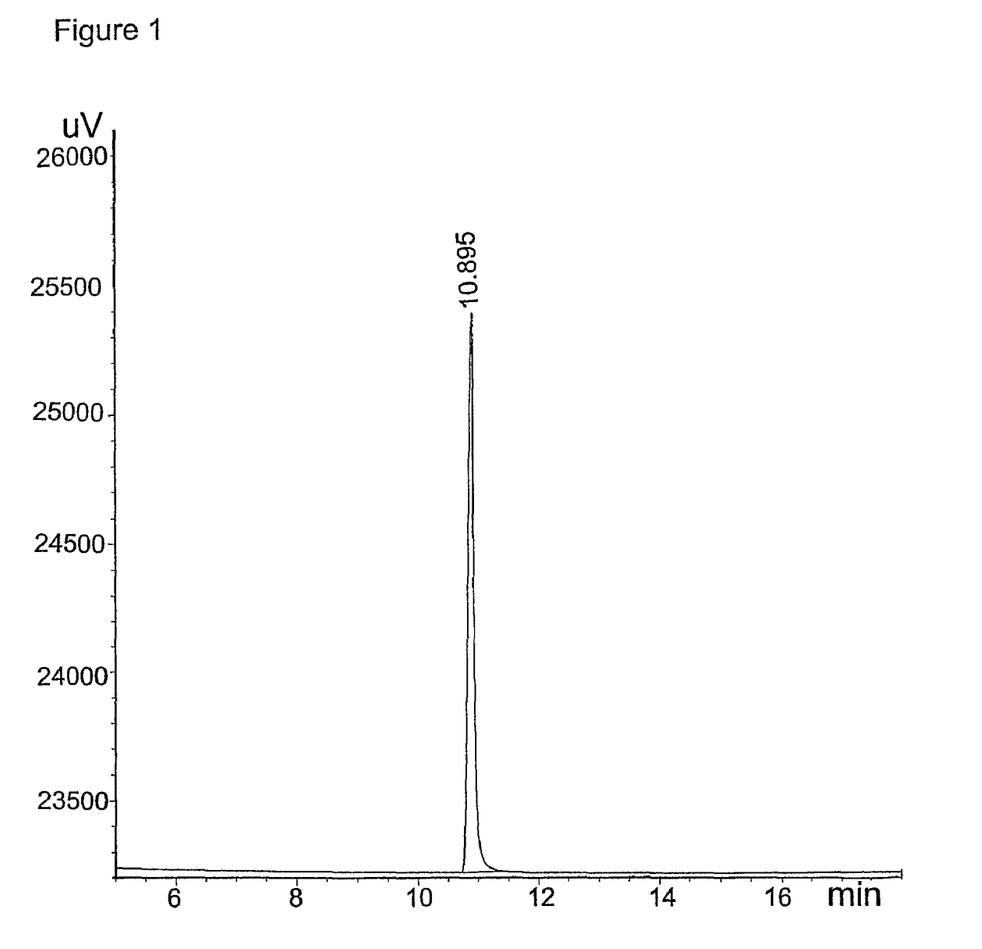
FIG. 1 is a GC of a commercially-available (−)-TDNF from Givaudan S A, Vernier, Switzerland.
Figure 2:
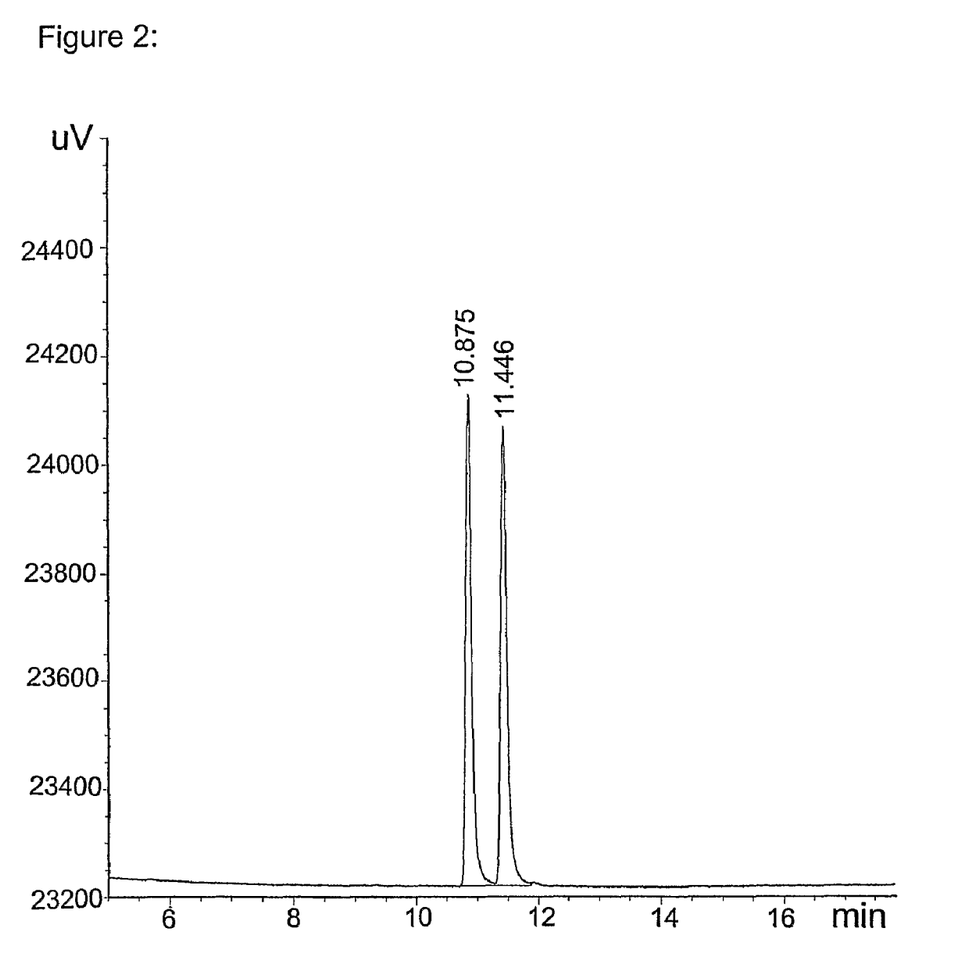
FIG. 2 is a GC of (rac)-TDNF, commercially available as Cetalox™ from Firmenich S A, Switzerland
Figure 3:
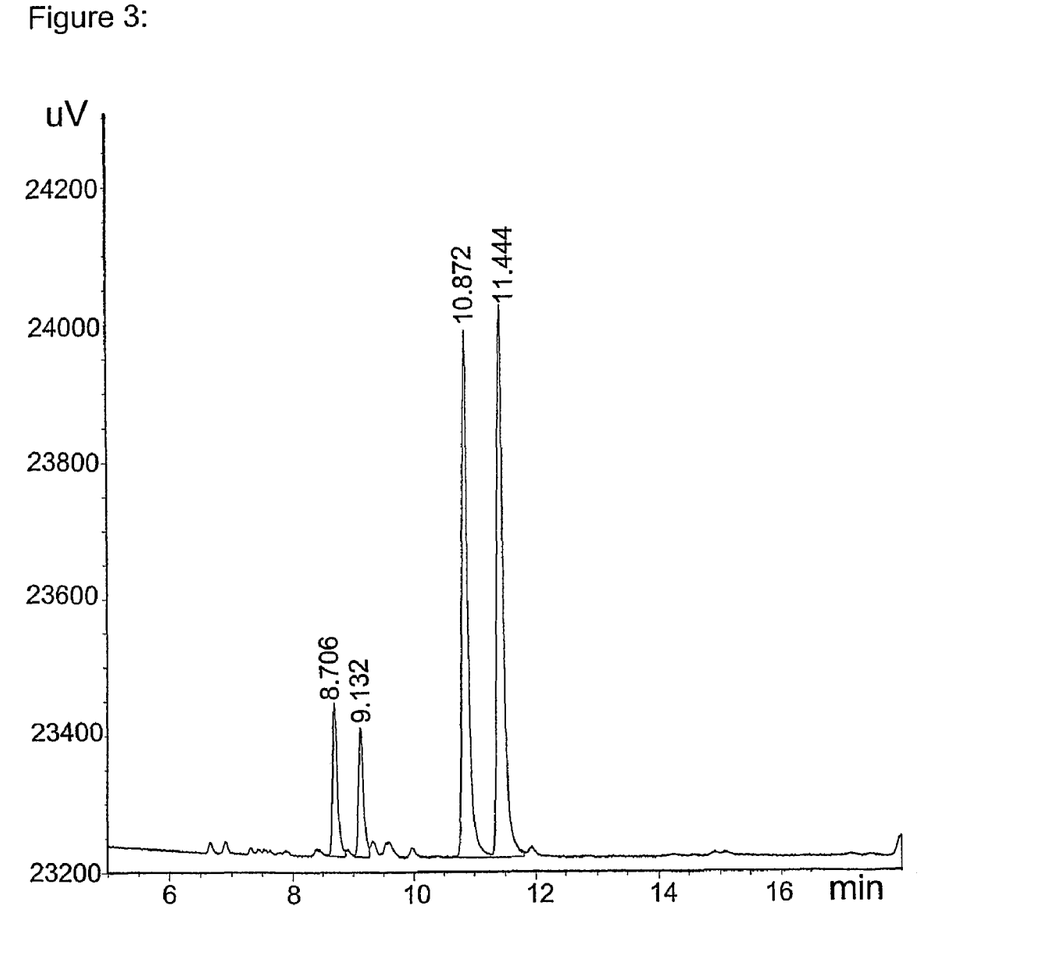
FIG. 3 is a GC of (−)-TDNF (7) and (+)-TDNF (8), obtained as 46:54 mixture as described in example 5 hereinunder.

Under an atmosphere of argon 6.0 g (15 mmol) (E,E)-4,8,12-trimethyl-trideca-3,7,11-trienoic acid (R)-methoxycarbonyl-phenyl-methyl ester (1), prepared from homofarnesic acid of 95% isomeric purity as described in example 1, were dissolved in 80 ml CH₂Cl₂ and 3 ml toluene. The solution was cooled to −75° C. and under cooling with liquid nitrogen a −70° C. cold solution of 3.5 ml (× eq.) of chlorosulphonic acid in 10 ml CH₂Cl₂ was added within 3 min. The reaction mixture was stirred at −70° C. for 10 min, quenched with 100 ml ice cold H₂O and diluted with 300 ml MTBE. The organic phase was separated, washed 3× with H₂O and once with 20% K₂HPO₄, dried over MgSO₄ and concentrated in vacuo. The crude residue (5.8 g) was dried in high vacuo, dissolved in 10 ml THF and added at r.t. to a suspension of 1.5 g LiAlH₄ in 40 ml THF such that the temperature was kept at 35-40° C. The reaction mixture was stirred at 40° C. for 30 min and hydrolised at 0-10° C. with 1.5 ml H₂O, 1.5 ml 15% NaOH and 4.5 ml H₂O. The mixture was stirred at 35° C. for 1 h, filtered and the residue washed with THF. The organic phase was dried over MgSO₄ and concentrated in vacuo. The residue, 4.79 g of a viscous oil, was purified by flash chromatography (120 silicagel, hexane/MTBE 1:1) to afford 0.83 g (25%, 2 steps) of alcohol 5/6 as a 4:1 mixture (NMR analysis). To a solution of 0.7 g (3 mmol) of the purified alcohol mixture 5/6 in 10 ml CH₂Cl₂ as added at r.t. 0.2 ml (3 mmol) methanesulphonic acid. The mixture was stirred for 1.5 h and diluted with 20 ml MTBE and 20 ml satd. KHCO₃ solution. The aqueous phase was extracted 2× with hexane, the combined organic phases were washed with satd. KHCO₃ solution, dried over MgSO₄ and concentrated in vacuo. The crude product (0.69 g) was purified by bulb to bulb distillation (110° C./0.05 Torr) to afford 0.49 g of a white solid. Analysis using a chiral column (Hydrodex-β-6TBDM, 25 m×0.25 mm, 170° C. isotherm, 60 kPa H₂, split 1:50) indicated a 46:54 mixture of (−)-TDNF (7) and (+)-TDNF (8), which is equal to an enantiomeric excess of 8%, (see FIG. 3).

EXAMPLE 6

4-Methyl-6-(2,6,6-trimethyl-cyclohex-1-enyl)-hex-3-enoic acid (S)-methoxycarbonyl-phenyl-methyl ester (11)

To a solution of 10.0 g (40 mmol) (E)-4-methyl-6-(2,6,6-trimethyl-cyclohex-1-enyl)-hex-3-enoic acid [H. S. Corey, J. R. D. Cormick, W. E. Swensen, *J. Am. Chem. Soc.* 1964, 86, 1884], isomeric purity of 95%, in 100 ml MTBE were added at r.t. 6.64 g (40 mmol) (S)-(+)-mandelic acid methyl ester $[\alpha]_D$=+144.9 (c=1.04, MeOH) and 1.0 g DMAP. Then a solution of 8.24 g (40 mmol) DCC in 100 ml MTBE was added and the reaction mixture stirred for 2 h. After addition of 1 ml MeOH and 1 ml HTDNF the mixture was stirred for 30 min, filtered and the residue washed with MTBE. The combined organic phases were concentrated in vacuo and the residue (18.0 g) was purified by flash chromatography (silicagel, hexane/MTBE 9:1) affording 14.0 g (88%) 4-methyl-6-(2,6,6-trimethyl-cyclohex-1-enyl)-hex-3-enoic acid (S)-methoxycarbonyl-phenyl-methyl ester (11) in form of a colorless oil.

IR(film): 2928 m, 1746 s, 1213 m, 1175 m, 1142 s, 1043 m.
¹H-NMR (400 MHz, CDCl₃): δ 0.99 (s, 6H), 1.41 (m, 2 H), 1.57 (m, 2H), 1.60 (s, 3 H), 1.68 (m, 3 H), 1.90 (t, J=6.3 Hz, 2H), 2.08 (s, 4H), 3.21 (m, 2H), 3.71 (s, 3H), 5.40 (t, J=7.1 Hz, 1H), 5.95 (s, 1H), 7.35-7.40 (m, 3H), 7.49-7.45 (m, 2 H) ppm.
¹³C-NMR (100 MHz, CDCl₃): δ 16.4 (q), 19.5 (t), 19.7 (q), 27.5 (t), 28.5 (2q), 32.7 (t), 33.2 (t), 34.9 (s), 39.8 (t), 40.0 (t), 52.5 (q), 74.4 (d), 114.3 (d), 127.1 (s), 127.5 (2d), 128.7 (2d), 129.1 (d), 133.8 (s), 136.8 (s), 140.5 (s), 169.2 (s), 171.6 (s) ppm.
MS (ESI-pos): 398 (8, [M]⁺), 250 (9), 249 (53), 150 (40), 149 (38), 137 (100), 136 (82), 121 (64), 95 (89), 81 (65).

EXAMPLE 7

4-Methyl-6-(2,6,6-trimethyl-cyclohex-1-enyl)-hex-3-enoic acid (R)-methoxycarbonyl-phenyl-methyl ester (12)

To a solution of 10.0 g (40 mmol) (E)-4-methyl-6-(2,6,6-trimethyl-cyclohex-1-enyl)-hex-3-enoic acid [H. S. Corey, J. R. D. Cormick, W. E. Swensen, *J. Am. Chem. Soc.* 1964, 86, 1884] in 100 ml MTBE were added at r.t. 6.64 g (40 mmol) (R)-(−)-mandelic acid methyl ester $[\alpha]_D$=−144.9 (c=1.04, MeOH) and 1.0 g DMAP. Then a solution of 8.24 g (40 mmol) DCC in 100 ml MTBE was added and the reaction mixture stirred for 3 h, filtered and the residue washed with MTBE. The combined organic phases were concentrated in vacuo and the residue (17.6 g) was purified by flash chromatography (250 g silicagel, hexane/MTBE 9:1) affording 12.2 g (88%) 4-methyl-6-(2,6,6-trimethyl-cyclohex-1-enyl)-hex-3-enoic acid (R)-methoxycarbonyl-phenyl-methyl ester (12) in form of a colorless oil.

IR (film): 2928 m, 1745 s, 1213 m, 1175 m, 1142 s, 1043 m.

$^1$H-NMR (400 MHz, CDCl$_3$): δ 0.99 (s, 6H), 1.41 (m, 2 H), 1.57 (m, 2H), 1.60 (s, 3 H), 1.68 (m, 3 H), 1.90 (t, J=6.3 Hz, 2H), 2.08 (s, 4H), 3.21 (m, 2H), 3.71 (s, 3H), 5.40 (t, J=7.1 Hz, 1H), 5.95 (s, 1H), 7.35-7.40 (m, 3H), 7.49-7.45 (m, 2 H) ppm.

$^{13}$C-NMR (100 MHz, CDCl$_3$): δ 16.4 (q), 19.5 (t), 19.7 (q), 27.5 (t), 28.5 (2q), 32.7 (t), 33.2 (t), 34.9 (s), 39.8 (t), 40.0 (t), 52.5 (q), 74.4 (d), 114.3 (d), 127.1 (s), 127.5 (2d), 128.7 (2d), 129.1 (d), 133.8 (s), 136.8 (s), 140.5 (s), 169.2 (s), 171.6 (s) ppm.

MS (ESI-pos): 398 (8, [M]$^+$), 249 (54), 189 (16), 137 (100), 136 (80), 121 (63), 107 (29), 95 (88), 81 (63).

EXAMPLE 8

Step 1) Synthesis of (S)-Phenyl-[(4aS,8aS)-2-(2,5,5,8a-tetramethyl-3,4,4a,5,6,7,8,8a-octahydro-naphthalen-1-yl)-acetoxy]-acetic acid methyl ester (9) and (S)-Phenyl-[(4aS,8aS)-2-(2,5,5,8a-tetramethyl-1,4,4a,5,6,7,8,8a-octahydro-naphthalen-1-yl)-acetoxy]-acetic acid methyl ester (10)

9

10

Under an atmosphere of argon 7.0 g (17.6 mmol) (E)-4-methyl-6-(2,6,6-trimethyl-cyclohex-1-enyl)-hex-3-enoic acid (S)-methoxycarbonyl-phenyl-methyl ester (11), prepared from monocyclohomofarnesic acid of 91% isomeric purity as described in example 6, was dissolved in 100 ml CH$_2$Cl$_2$. The solution was cooled to −90° C. and under cooling with liquid nitrogen 4.2 ml (3.7 eq.) chlorosulphonic acid was added such that the reaction temperature did not exceed −80° C. After complete addition the reaction mixture was kept at −80° C. for 30 min and then poured rapidly onto 100 ml satd. KHCO$_3$ solution. The mixture was extracted 2× with MTBE, the combined organic phases were washed 2× with satd. KHCO$_3$ solution, dried over MgSO$_4$ and concentrated in vacuo. The crude residue (6.34 g) was purified by flash chromatography (200 silicagel, hexane/MTBE 9:1) to afford 5.0 g (71%) of a mixture of ester 9/10, which was used directly in the next step.

Step 2) (4aS,8aS)-2-(2,5,5,8a-Tetramethyl-3,4,4a,5,6,7,8,8a-octahydro-naphthalen-1-yl)-ethanol (5) and (4aS,8aS)-2-(2,5,5,8a-Tetramethyl-1,4,4a,5,6,7,8,8a-octahydro-naphthalen-1-yl)-ethanol (6)

5

6

To a suspension of 1.0 g (26 mmol) LiAlH$_4$ in 50 ml THF was added at 20° C. a solution of 5.0 g (12.6 mmol) ester mixture 3/4 (example 8, step 1) dissolved in 10 ml THF, during which the temperature raised to 40° C. The reaction mixture was kept at 40° C. for 1 h, and carefully hydrolysed with 1 ml H$_2$O. Then 1 ml 15% NaOH solution was added and the mixture stirred for 5 min. After addition of 2 ml H$_2$O stirring was continued for 20 min and the mixture was filtered. The residue was washed with MTBE, the combined organic phases were dried over MgSO$_4$ and concentrated in vacuo. The crude product was purified by flash chromatography (silicagel, hexane/MTBE 9:1) to give 2.2 g alcohol mixture of 5/6 (5:1, GC analysis) that was directly used in the next step.

Step 3) Synthesis of (−)-TDNF (7) and (+)-TDNF (8)

To a solution of 1.9 g alcohol mixture 5/6 (example 8, step 2) in 20 ml CH$_2$Cl$_2$ was added at r.t. and under an atmosphere of nitrogen 1 ml methanesulfonic acid. The mixture was stirred for 30 min and poured onto 100 ml satd. KHCO$_3$ solution. The aqueous phase was extracted 2× with MTBE, the combined organic phases were washed 1× with satd. KHCO$_3$ solution and 1× with brine, dried over MgSO$_4$ and concentrated in vacuo. The crude product (1.84 g) was purified by flash chromatography (50 g silicagel, hexane/MTBE 49:1) to afford 1.13 g of a white solid. Analysis using a chiral column (Hydrodex-B-6-TBDM, 25 m×0.25 mm, 170° C. isotherm, 60 kPa H$_2$, split 1:50) indicated a 47:53 mixture of (−)-TDNF (7) and (+)-TDNF (8), which is equal to an enantiomeric excess of 6%.

EXAMPLE 9

Step 1) Synthesis of (S)-Phenyl-[(4aS,8aS)-2-(2,5,5,8a-tetramethyl-3,4,4a,5,6,7,8,8a-octahydro-naphthalen-1-yl)-acetoxy]-acetic acid methyl ester (9) and (S)-Phenyl-[(4aS,8aS)-2-(2,5,5,8a-tetramethyl-1,4,4a,5,6,7,8,8a-octahydro-naphthalen-1-yl)-acetoxy]-acetic acid methyl ester (10)

Under an atmosphere of argon 6.0 g (15.0 mmol) 4-methyl-6-(2,6,6-trimethyl-cyclohex-1-enyl)-hex-3-enoic acid (S)-methoxycarbonyl-phenyl-methyl ester (11), prepared from monocyclohomofarnesic acid of 91% isomeric purity as described in example 6, was dissolved in 45 ml CH$_2$Cl$_2$. The solution was cooled to −35° C. and under cooling 1.5 ml (1.75 eq.) H$_2$SO$_4$ conc. was added such that the reaction temperature did not exceed −30° C. After complete addition the reaction mixture was kept at −25° C. for 30 min and then poured rapidly onto 100 ml satd. KHCO$_3$ solution. The mixture was extracted 2× with MTBE, the combined organic phases were washed 1× with satd. KHCO$_3$ solution, dried over MgSO$_4$ and concentrated in vacuo. The crude residue (5.46 g) was purified by flash chromatography (200 silicagel, hexane/MTBE 9:1) to afford 3.2 g (53%) of an ester mixture 9/10, which was used directly in the next step.

Step 2) (4aS,8aS)-2-(2,5,5,8a-Tetramethyl-3,4,4a,5,6,7,8,8a-octahydro-naphthalen-1-yl)-ethanol (5) and (4aS,8aS)-2-(2,5,5,8a-Tetramethyl-1,4,4a,5,6,7,8,8a-octahydro-naphthalen-1-yl)-ethanol (6)

To a suspension of 1.0 g (26 mmol) LiAlH$_4$ in 40 ml THF was added at 20° C. a solution of 3.0 g (7.5 mmol) ester mixture 3/4 (example 9, step 1) dissolved in 10 ml THF, during which the temperature raised to 40° C. The reaction mixture was kept at 40° C. for 1 h, and carefully hydrolysed with 1 ml H$_2$O. Then 1 ml 15% NaOH solution was added and the mixture stirred for 5 min. After addition of 2 ml H$_2$O stirring was continued for 20 min and the mixture was filtered. The residue was washed with MTBE, the combined organic phases were dried over MgSO$_4$ and concentrated in vacuo. The crude product was purified by flash chromatography (silicagel, hexane/MTBE 9:1) to give 1.1 g alcohol mixture of 5/6 (4:1, GC analysis) that was directly used in the next step.

Step 3) Synthesis of (−)-TDNF (7) and (+)-TDNF (8)

To a solution of 0.7 g alcohol mixture 5/6 (example 9, step 2) in 10 ml CH$_2$Cl$_2$ was added at r.t. and under an atmosphere of nitrogen 1 ml methanesulfonic acid. The mixture was stirred for 2 h and poured onto 20 ml satd. KHCO$_3$ solution. The aqueous phase was extracted 2× with MTBE, the combined organic phases were washed 1× with satd. KHCO$_3$ solution and 1× with brine, dried over MgSO$_4$ and concentrated in vacuo. The crude product (0.5 g) was analyzed by GC (chiral column hydrodex-B-6-TBDM, 25 m×0.25 mm, 170° C. isotherm, 60 kPa H$_2$, split 1:50) indicating a 44:56 mixture of (−)-TDNF (7) and (+)-TDNF (8), which is equal to an enantiomeric excess of 12%.

The invention claimed is:
1. A method of preparation of a (±)-3a,6,6,9a-tetramethyl-dodecahydro-naphtho[2,1b]furan ("TDNF") mixture having a proportion of one isomer greater than 50%, comprising the steps of:
   1. reacting a compound selected from (E,E)-homofarnesic acid and (E)-monocyclohomofarnesic acid with a chiral alcohol of formula R*OH, wherein the chiral alcohol R*OH is of formula in which:

R¹, R² and R³ are individually selected from H, alkyl, alkenyl, alkinyl, cycloakyl, cycloalkenyl, cycloalkylalkyl, alkylcycloakyl, cycloakylalkenyl, alkylcycloalkenyl, aryl, alkylaryl, alkenylaryl, arylalkyl, arylalkenyl and cyclic moieties of these types that include at least one heteroatom, preferably selected from N, O, S, Si, R¹, R² and R³ optionally additionally comprising at least one substituent preferably selected from OH, CHO, $CO_2H$, $CO_2R^4$, $CONH_2$, $CONHR^5$, $CONR^5R^6$, $NO_2$, CN; $R_4$, $R_5$ and $R_6$ being independently $C_1$-$C_6$ alkyl;

with the proviso that the residues R¹, R² and R³ are different, to form a compound selected from the group consisting of compounds of formula III and formula IV:

wherein R* is the residue of a chiral alcohol R*OH, 2. reacting the result of step 1 with an acid to form one of the compounds of formula V 3. reacting the result of step 2 with a reducing agent, to form an alcohol; and
4. treating the alcohol of step 3 with an acid to form compounds of the formulae VI and VII

* * * * *